United States Patent [19]
Timmons et al.

[11] Patent Number: 5,948,432
[45] Date of Patent: Sep. 7, 1999

[54] KERATIN-BASED SHEET MATERIAL FOR BIOMEDICAL APPLICATIONS AND METHOD OF PRODUCTION

[75] Inventors: Scott F. Timmons; Cheryl R. Blanchard, both of San Antonio, Tex.; Robert A. Smith, Jackson, Miss.

[73] Assignee: Keraplast Technologies Ltd., San Antonio, Tex.

[21] Appl. No.: 08/979,526

[22] Filed: Nov. 26, 1997

[51] Int. Cl.[6] .............................. A61K 9/70; A61K 38/00; A01N 25/34; A61L 15/00
[52] U.S. Cl. .......................... 424/443; 424/402; 424/445; 514/21; 525/54.1; 530/355
[58] Field of Search ....................... 424/402, 443, 424/445; 530/355; 514/21; 525/54.1

[56] References Cited

U.S. PATENT DOCUMENTS

| | | | |
|---|---|---|---|
| 4,135,942 | 1/1979 | Kikkawa | 106/155 |
| 4,570,629 | 2/1986 | Widra | 128/156 |
| 5,047,249 | 9/1991 | Rothman et al. | 424/543 |
| 5,358,935 | 10/1994 | Smith et al. | 514/21 |
| 5,639,448 | 6/1997 | Galleguillos et al. | 424/70.11 |
| 5,712,252 | 1/1998 | Smith | 514/21 |
| 5,763,583 | 6/1998 | Arai et al. | 530/353 |

*Primary Examiner*—Jose' G. Dees
*Assistant Examiner*—Marina Lamm
*Attorney, Agent, or Firm*—Crompton, Seager & Tufte

[57] ABSTRACT

A sheet wound dressing formed of cross linked keratin. An insoluble, largely Beta keratin fraction from human hair is acidified to a low pH, preferably less than about 3, which partially solubilizes the keratin by weakening hydrogen bonds. The suspension is added to base, such as ammonium hydroxide, forming a slurry. The slurry is cast directly onto a flat surface, allowing the re-formation of cross-links including hydrogen bonds and disulfide bonds. The resulting cross-linked keratin sheet can be used as a sheet wound dressing or as a scaffolding for growth of cells. The insoluble keratin can be derived from human hair which is washed, rinsed, dried, chopped and treated with peracetic acid to break some accessible disulfide linkages. The treated hair is filtered, rinsed, dried, and ground into a keratin powder. The keratin powder is suspended in a mixture of ammonium hydroxide and ammonium thioglycollate and heated sufficiently to dissolve the soluble keratin fraction, followed by cooling and centrifugation to concentrate the insoluble, largely Beta keratin fraction.

33 Claims, No Drawings

KERATIN-BASED SHEET MATERIAL FOR BIOMEDICAL APPLICATIONS AND METHOD OF PRODUCTION

CROSS-REFERENCE TO RELATED APPLICATIONS

The present application is related to U.S. patent application Ser. No. 08/979,456, filed on date even herewith, entitled KERATIN-BASED HYDROGEL FOR BIOMEDICAL APPLICATIONS AND METHOD OF PRODUCTION. The present application is also related to U.S. Pat. No. 5,358,935, entitled NONANTIGENIC KERATINOUS PROTEIN MATERIAL, both herein incorporated by reference.

FIELD OF THE INVENTION

The present invention is related to wound dressing materials and tissue engineering scaffolds. More specifically, the present invention is related to a cross-linked keratin sheet material.

BACKGROUND OF THE INVENTION

Chronic wounds can be caused by a variety of events, including surgery, prolonged bedrest and traumatic injuries. Partial thickness wounds can include second degree burns, abrasions, and skin graft donor sites. Healing of these wounds can be problematic, especially in cases of diabetes mellitus or chronic immune disorders. Full thickness wounds have no skin remaining, and can be the result of trauma, diabetes (e.g., leg ulcers) and venous stasis disease, which can cause full thickness ulcers of the lower extremities. Full thickness wounds tend to heal very slowly. Proper wound care technique including the use of wound dressings is extremely important to successful chronic wound management. Chronic wounds affect an estimated four million people a year, resulting in health care costs in the billions of dollars. "Treatment of Skin Ulcers with Cultivated Epidermal Allografts," T. Phillips, O. Kehinde, and H. Green, *J. Am. Acad. Dermatol.*, V. 21, pp. 191–199 (1989).

The wound healing process involves a complex series of biological interactions at the cellular level which can be grouped into three phases: hemostasis and inflammation; granulation tissue formation and reepithelization; and remodeling. "Cutaneous Tissue Repair: Basic Biological Considerations,", R. A. F. Clark, *J. Am. Acad. Dermatol.*, Vol. 13, pp. 701–725 (1985). Keratinocytes (epidermal cells that manufacture and contain keratin) migrate from wound edges to cover the wound. Growth factors such as transforming growth factor-β (TGF-β) play a critical role in stimulating the migration process. The migration occurs optimally under the cover of a moist layer. Keratins have been found to be necessary for reepithelization. Specifically, keratin types K5 and K14 have been found in the lower, generating, epidermal cells, and types K1 and K10 have been found in the upper, differentiated cells. Wound Healing: Biochemical and Clinical Aspects, I. K. Cohen, R. F. Diegleman, and W. J. Lindblad, eds., W. W. Saunders Company, 1992. Keratin types K6 and K10 are believed to be present in healing wounds, but not in normal skin. Keratins are major structural proteins of all epithelial cell types and appear to play a major role in wound healing.

An optimum wound dressing would protect the injured tissue, maintain a moist environment, be water permeable, maintain microbial control, deliver healing agents to the wound site, be easy to apply, not require frequent changes and be non-toxic and non-antigenic. Although not ideal for chronic wounds, several wound dressings are currently on the market, including occlusive dressings, non-adherent dressings, absorbent dressings, and dressings in the form of sheets, foams, powders and gels. Wound Management and Dressing, S. Thomas, The Pharmaceutical Press, London, 1990.

Attempts have been made to provide improved dressings that would assist in the wound healing process using biological materials such as growth factors. To date, these biologicals have proven very costly and shown minimal clinical relevance in accelerating the chronic wound healing process. In cases of severe full thickness wounds, autografts (skin grafts from the patient's body) are often used. Although the graft is non-antigenic, it must be harvested from a donor site on the patient's body, creating an additional wound. In addition, availability of autologous tissue may not be adequate. Allografts (skin grafts from donors other than the patient) are also used when donor sites are not an option. Allografts essentially provide a "wound dressing" that provides a moist, water permeable layer, but is rejected by the patient usually within two weeks and does not become part of the new epidermis.

What would be desirable and has not heretofore been provided is a wound dressing that protects the injured tissue, maintains a moist environment, is water permeable, is easy to apply, does not require frequent changes and is non-toxic and non-antigenic, and most important, delivers effective healing agents to the wound site.

Tissue engineering is a rapidly growing field encompassing a number of technologies aimed at replacing or restoring tissue and organ function. The consistent success of a tissue engineered implant rests on the invention of a biocompatible, mitogenic material that can successfully support cell growth and differentiation and integrate into existing tissue. Such a scaffolding material could greatly advance the state of the tissue engineering technologies and result in a wide array of tissue engineered implants containing cellular components such as osteoblasts, chondrocytes, keratinocytes, and hepatocytes to restore or replace bone, cartilage, skin, and liver tissue respectively.

SUMMARY OF THE INVENTION

The present invention includes a sheet formed of cross-linked keratin not requiring a binding agent. The sheet is believed to be bound together by reformed disulfide linkages and hydrogen bonds. A preferred use of the sheet is as a wound healing dressing. Another preferred use is as a tissue engineering cell scaffold for implant applications. The sheet can be formed from an insoluble protein fraction derived from hair, the fraction containing primarily Beta keratin. Keratin can be obtained from a number of sources including human or animal hair, and finger or toe nails, with one source being hair of the patient or a donor.

The sheet can be formed by providing an insoluble keratin fraction suspended in water, and lowering the pH until the keratin protein is partially unfolded. Partially unfolded is defined as the protein molecule unfolding at one end such that the resulting suspension of keratin particles behaves like a colloidal suspension. In one method, concentrated sulfuric acid is added until a pH of less than 1 is reached. Applicants believe the low pH disrupts the hydrogen bonds which have been rendering the keratin fraction insoluble, thereby allowing the protein to partially unfold. The partially unfolded keratin is then made basic with ammonium hydroxide. This treatment exchanges the non-volatile acid with a volatile base, which is removed upon drying. Alternatively, a volatile acid, such as formic acid, may be employed, eliminating the requirement for further treatment with a volatile base. The resulting slurry can then be cast onto a flat surface or mold of appropriate geometry and surface finish and air dried to produce a cross-linked keratin sheet. Applicants believe the cross-links result from the thiol groups re-forming disulfide linkages and from the sulfonic acid, amines and carboxylic acid groups forming hydrogen bonds.

The resulting sheet is thus formed of pure keratin. Keratin has been shown to be biocompatible, non-immunogenic, not to inhibit activated T-cells and therefore not interfere with the normal cell mediated immune response, and to be mitogenic for keratinocytes, fibroblasts, and human microvascular endothelial cells. Keratin has also been shown to promote epithelialization in wound healing studies on rats and humans.

The moist keratin sheet has the consistency of moist, thick paper. The sheet dries to a brittle material which can be rehydrated to a supple, skin-like material. The rehydrated sheet has the look and feel of skin while retaining moisture within the sheet and within the wound. The sheet can be used as a wound healing dressing or as a cell growth scaffold. The sheet can be cut and shaped as needed before being applied to the wound. The keratin sheets provide a non-antigenic wound dressing that maintains wound moisture for migrating epithelial cells and provides a scaffold for cell growth for tissue engineered implants. Other applications for this keratin sheet include use as diffusion membranes and as an encapsulant for cells for various biomedical applications.

DETAILED DESCRIPTION OF THE PREFERRED EMBODIMENTS

In a method according to the present invention, hair is provided, preferably washed and unbleached. The hair is harvested from a human or animal source. The patient or a human donor is a preferred source of hair, as hair from these sources is most likely to result in a non-antigenic wound healing product, although animal hair may be acceptable for certain individuals that do not have animal product allergy problems. In one method, the hair is washed with Versa-Clean™ (Fisher Scientific, Pittsburgh, Pa.), rinsed with deionized water, and allowed to air dry.

The hair can be oxidized in peracetic acid or another suitable reagent such as $H_2O_2$. A preferable treatment utilizes from 1% to 32% peracetic acid, at a temperature between about 0° C. and 100° C. for between 0.5 and 24 hours. One method treats 30 grams of hair with 500 mL of 32% peracetic acid at 4° C. for 24 hours. This treatment with peracetic acid partially oxidizes the naturally occurring disulfide linkages to produce a protein with cysteic acid ($-CH_2SO_3H$) residues and remaining disulfide linkages. The hair is recovered, preferably by filtration through a coarse fritted glass filter, and rinsed numerous times with deionized water until the rinse solution has a pH of 6.0 or higher. The hair can then be dried in a vacuum oven at between 20° C. and 50° C. for between 0.5 and 5 days. One method dries the hair in a vacuum oven at 40° C. for several days. The dried hair can then be pulverized and ground into a fine powder. One method of grinding the hair uses a ceramic mortar and pestle.

The keratin powder can be suspended in ammonium thioglycollate. In one method, pulverized keratin powder, derived from hair as described above, is suspended in about 3N ammonium hydroxide containing ammonium thioglycollate. About six grams of keratin powder can be added per 75 mL of ammonium hydroxide. The strength of ammonium hydroxide is preferably about 3N and the preferred concentration of ammonium thioglycollate is about 11 mL (as thioglycollic acid) per 75 mL of ammonium hydroxide. The suspension can then be heated for a time sufficient to solubilize the soluble fraction of the hair. The suspension, in one method, is heated between 50° and 90° C. for between 1 and 24 hours, followed by cooling. According to another method, the suspension is heated to about 60° C. for about 4 hours and cooled to room temperature. This treatment cleaves the remaining disulfide linkages to produce cysteine residues in the protein structure. At this point, the keratin protein contains both cysteic acid residues and cysteine residues. The ratio of cysteic acid residues and cysteine residues can be controlled by varying the time, temperature, and concentration of oxidant in the peracetic acid treatment step previously described. The presence of sulfonic acid residues imparts a hydrophilic property to the hair as well as the final sheet product.

After the oxidation/reduction treatment described above, a resistant keratin fraction remains, consisting primarily of Beta keratin. This keratin fraction is preferably at least 80% Beta-keratin, most preferably greater than about 90% Beta keratin. This fraction is insoluble in the suspension and is removed in one method by centrifugation at about 10,000 g for about 10 minutes. A thick, jelly-like supernatant remains and is discarded, or more preferably kept for another use. The remaining insoluble fraction is composed mostly of the original cuticle (outer layer of hair shaft) and is composed primarily of Beta keratin.

The insoluble material is transferred to another container and acidified to a low pH. The pH is preferably less than about 3 and most preferably less than about 1. In one method the pH is less than about 1 and the acid used can be either concentrated sulfuric acid or formic acid. This treatment disrupts hydrogen bonding of the cuticle structure of the hair shaft. The low pH disrupts the hydrogen bonds responsible for tightly binding the keratin protein, resulting in its resistance to chemical modification. Applicants believe the acid at least partially unfolds the protein, enhancing the solubility. The slurry preferably has a concentration in the range of 0.001 grams/mL to 6 grams/mL. The slurry most preferably has a concentration in the range of 0.2 grams/mL to 0.3 grams/mL.

The unfolded keratin slurry can then be made slightly basic with ammonium hydroxide, preferably about 6N strength. The slurry can then be cast onto a flat surface and air-dried to produce the crosslinked sheet. A preferred relative humidity range for drying is between 0% and 90%. The relative humidity is most preferably between about 40% and 60% relative humidity. The partially unfolded, partially solubilized keratin refolds upon addition of the base during drying, causing hydrogen bonding of the keratin. The free thiol groups form disulfide linkages.

The insoluble keratin fraction from hair is thus treated so as to have both sulfonic acid groups and thiol groups, and is separated from the soluble fraction. The insoluble fraction is treated with acid to partially unfold and solubilize the keratin, followed by treatment with base and casting onto a flat surface to refold the protein and form some disulfide bonds.

In an alternate method, in the acidification step, the keratin is suspended in a volatile acid, such as formic acid, having sufficiently low pH to partially unfold the keratin protein. In this method, the treatment with volatile base can be dispensed with. The acidification step can be immediately followed by forming the keratin slurry into a sheet.

The resulting sheet may be cleansed of soluble reagents by repeated treatment with hot (boiling), deionized water, yielding a cross-linked, pure keratin sheet. The moist keratin sheet has the consistency of moist paper. The sheet produced will dry to a brittle material which can be rehydrated to a supple skin-like material, suitable for use as a sheet wound dressing. The sheet retains water and the rehydrated sheet has the look and feel of skin. In a preferred method of use, the sheet is hydrated sufficiently to allow the sheet to be draped over a wound.

Applicants believe the keratin product made according to this method is suitable for use as a cell growth scaffold that is mitogenic and as a nutrient support for cell growth. Applicants also believe the cross-linked keratin sheet can be used as a scaffold material for a variety of cells including skin component cells (keratinocytes, fibroblasts, endothelial cells), osteoblasts, chondrocytes, and hepatocytes. In particular, applicants have shown that skin component cells will grow and proliferate favorably on the keratin sheet. Applicants further believe the keratin sheet can be used as a diffusion membrane and to encapsulate cells for various applications.

Anti-bacterial additives, ointments and biologicals such as growth factors or collagen can be added to the keratin sheet. Bactericidal ointment or a suspension of antibiotics or biologicals can be impregnated into the sheet dressing by passing a blade having the additive at its front over the sheet, thereby evenly distributing the additive over the sheet. Alternatively, the sheet material can be soaked in a solution containing the desired additive and the additive allowed to precipitate onto the surface of the sheet. The solvent can then be flashed off, leaving the sheet material impregnated and coated with the desired additive.

EXPERIMENTAL RESULTS

A sheet wound dressing not requiring a binder was prepared from keratin derived from human hair. Human hair was obtained from males aged 12 to 20 years, washed with Versa-Clean™ (Fisher Scientific, Pittsburgh, Pa.), rinsed with deionized water and allowed to air dry. This hair was subsequently chopped into approximately 0.25 inch to 2 inch lengths using shears. Thirty grams of this hair was treated with 500 mL of 32% peracetic acid (Aldrich Chemical, Milwaukee, Wis.) at 4° C. for 24 hours. This treatment partially oxidized the disulfide linkages. The hair was recovered by filtration through a coarse fritted glass filter and rinsed numerous times with deionized water until the rinse solution was pH 6.0 or higher. The hair was dried under vacuum at 40° C. for several days until completely dry and ground to a fine powder with a ceramic mortar and pestle. The resulting material, 19 grams, was further modified to produce a flexible, hydratable sheet composed primarily of Beta-keratin.

Six grams of the pulverized, oxidized hair was suspended in 75 mL of 3N ammonium hydroxide containing 11 mL of ammonium thioglycollate (as thioglycollic acid). The suspension was heated to 60° C. for 4 hours and then cooled to room temperature. This treatment cleaved the remaining disulfide linkages to produce cysteine residues in the protein structure. An insoluble fraction remained which was resistant to solubilization by the ammonium hydroxide and ammonium thioglycollate. The insoluble fraction, comprised mostly of Beta-keratin, was isolated by centrifugation at 10,000 g for 10 minutes. A thick, jelly-like supernatant was removed from the centrifuged material and set aside.

The remaining, insoluble fraction is composed mostly of the original cuticle (outer layer of hair shaft) and is composed primarily of Beta-keratin. The insoluble material was transferred to a flask and acidified to a pH of between 0 and about 1 with concentrated sulfuric acid. The partially unfolded keratin was made slightly basic with 6N ammonium hydroxide. The slurry was then cast onto a flat surface and air-dried to produce a cross-linked sheet. The resulting sheet was purified by immersion in boiling water which removed soluble reagents.

The use of keratin-containing materials in promoting wound healing was demonstrated in several experiments. In a first experiment, processed human hair was incubated with cell culture media. The media/hair mixture was passed through a micro filter. Cell lines relevant to wound healing, including human microvascular endothelial cells, keratinocytes and fibroblasts, were placed in culture using this media extract. Significant proliferation of these wound healing cells was measured. Keratinocytes proliferated profusely, fibroblasts proliferated modestly, and endothelial cells proliferated profusely.

The mitogenic activity observed in fibroblast, keratinocyte, and endothelial cell cultures is additional evidence that the keratinous protein material is not only biocompatible but also mitogenic with these cell lines. Additional biocompatibility was observed when keratin microfibrils were observed microscopically to be in direct contact with cells in the cell cultures. Specifically, keratinocytes and fibroblasts were observed to adhere to and congregate around microfibrils indicating that desirous cell activity can be sustained on this naturally derived biopolymer matrix.

In a second experiment, processed human hair powder was incubated with cell culture media. The media/keratin mixture was passed through a micro filter. This media extract was used in proliferation studies with lymphocytes. The lymphocyte cell line did not proliferate, indicating the material to be non-immunogenic.

In a third experiment, processed human hair powder was incubated with cell culture media. The media/hair mixture was then passed through a micro filter. This media extract was used in proliferation studies with activated T-lymphocytes. The T-lymphocytes proliferated normally, indicating no inhibition of the normal cell mediated immune response by the keratin. This demonstrated no inhibition of this very important function of immune cells.

In a fourth experiment, human hair was chemically treated as previously described. This produced a keratin slurry that was then cast into a sheet and chemically crosslinked to produce a non-soluble sheet of keratin. Segments of the sheeting were then incubated with keratinocytes, fibroblasts and human microvascular endothelial cells. These cells were shown to grow and proliferate favorably on the keratin sheet. This indicates that skin component cells proliferate favorably in the presence of keratin sheeting produced by the above described method.

In a fifth experiment, twenty-eight hairless rats were wounded on either side of the dorsal midline with a dermatome, creating a partial thickness wound, 0.12 inches in depth, and 2.0×4.0 cm in surface area. Half the wounds were treated with keratin powder, half were not, and both halves were covered with polyurethane dressing. The wounds were observed for healing and biopsied at days 0, 2, 4 and 6 for histochemical analysis. Planimetry studies showed 97% epithelialization of the keratin treated wounds and 78% epithelialization of the non-treated wounds at day 4. Histological analysis by H & E stain revealed total epithelialization microscopically of the keratin treated wounds at day 2 and only partial epithelialization of the non-treated wounds at day 2. Histological analyses at days 4 and 6 also revealed an acceleration of the epithelialization maturation process in the keratin treated wounds.

Human clinical studies are currently being performed on donor sites for skin grafts. One half of the donor wound site is treated with sterilized keratin powder and the opposite half treated in a standard fashion, with Adaptic™ non-adhering dressing from Johnson & Johnson. Preliminary results show the keratin treated halves epithelialize sooner and mature more rapidly. This was confirmed through both clinical observations and histological results of 4 millimeter punch biopsies. Subjectively, patients also have much less pain in the keratin treated wounds.

Numerous characteristics and advantages of the invention covered by this document have been set forth in the foregoing description. It will be understood, however, that this disclosure is, in many respects, only illustrative. Changes may be made in details, particularly in matters of shape, size, and ordering of steps without exceeding the scope of the invention. The invention's scope is, of course, defined in the language in which the appended claims are expressed.

What is claimed is:

1. A sheet wound dressing comprising a keratin sheet having added hydrophilic groups bound to said keratin, wherein said keratin sheet is bound together with bonds consisting essentially of keratin to keratin bonds.

2. A sheet wound dressing as recited in claim 1, wherein said keratin sheet includes water.

3. A sheet wound dressing as recited in claim 1, wherein said keratin is cross-linked without a binder.

4. A sheet wound dressing as recited in claim 1, wherein said keratin comprises primarily Beta keratin.

5. A sheet wound dressing as recited in claim 1, wherein said keratin is derived from vertebrate hair.

6. A sheet wound dressing as recited in claim 5, wherein said keratin is derived from human hair.

7. A sheet wound dressing as recited in claim 5, wherein said keratin is derived primarily from the cuticle structure of hair shafts.

8. A keratin sheet as recited in claim 1, wherein said added hydrophilic groups include sulfonic acid groups formed from oxidized disulfide bonds.

9. A process for forming a sheet wound dressing comprising the steps of:
   providing a keratin fraction insoluble in water at neutral pH and room temperature;
   suspending said keratin fraction in an acid having sufficiently low pH to at least partially unfold said keratin, thereby forming a keratin suspension;
   adding a base to said keratin suspension, thereby creating a keratin slurry; and
   forming said keratin slurry into a sheet.

10. A process for forming a sheet wound dressing as recited in claim 9 wherein said keratin fraction is insoluble in water at all pHs between 1 and 14.

11. A process for forming a sheet wound dressing as recited in claim 9 wherein said insoluble keratin fraction remains insoluble after oxidation with peracetic acid and reduction with alkaline ammonium thioglycollate.

12. A process for forming a sheet wound dressing as recited in claim 9, wherein said forming step includes casting said slurry onto a flat surface.

13. A process for forming a sheet wound dressing as recited in claim 9, wherein said keratin slurry has a pH greater than about 6.

14. A process for forming a sheet wound dressing as recited in claim 9, wherein said keratin is derived from human hair.

15. A process for forming a sheet wound dressing as recited in claim 9, wherein said acid is selected from the group consisting of concentrated sulfuric acid and formic acid and having a pH less than about 6.

16. A process for forming a sheet wound dressing as recited in claim 9, wherein said base is ammonium hydroxide having a concentration of at least $1 \times 10^{-5}$ M.

17. A process for forming a sheet wound dressing comprising the steps of:
   providing a keratin fraction insoluble in water at room temperature at all pHs between 1 and 14;
   suspending said keratin fraction in a volatile acid having sufficiently low pH to partially unfold said keratin protein, such that a slurry is formed; and
   forming said keratin slurry into a sheet.

18. A process for forming a sheet wound dressing comprising the steps of:
   providing a keratin fraction insoluble in water at room temperature at all pHs between 1 and 14;
   suspending said keratin fraction in a non-volatile acid having sufficiently low pH to partially unfold said keratin protein, such that a slurry is formed;
   exchanging the non-volatile acid by treatment with a volatile base; and
   forming said keratin slurry into a sheet.

19. A keratin sheet formed by the steps comprising:
   providing a keratin fraction insoluble in water at room temperature and neutral pH;
   suspending said keratin fraction in an acid having sufficiently low pH to partially unfold said keratin, thereby forming a keratin suspension;
   adding a base to said keratin suspension, thereby creating a keratin slurry; and
   forming said keratin slurry into a sheet.

20. A keratin sheet as recited in claim 19, wherein said keratin is primarily Beta keratin.

21. A keratin sheet as recited in claim 19 wherein said keratin fraction is insoluble in water at all pHs between 1 and 14.

22. A keratin sheet as recited in claim 19 wherein said insoluble keratin fraction remains insoluble after oxidation with peracetic acid and reduction with alkaline ammonium thioglycollate.

23. A keratin sheet as recited in claim 19, wherein said suspension has a pH less than about 6.

24. A keratin sheet as recited in claim 19, wherein said slurry has a pH greater than about 7.

25. A keratin sheet formed by the steps comprising:
   providing a keratin fraction insoluble in water at room temperature at all pHs between 1 and 14;
   suspending said keratin fraction in a volatile acid having sufficiently low pH to partially unfold said keratin protein, such that a slurry is formed; and
   forming said keratin slurry into a sheet.

26. A keratin sheet formed by the steps comprising:
   providing a keratin fraction insoluble in water at room temperature at all pHs between 1 and 14;
   suspending said keratin fraction in a non-volatile acid having sufficiently low pH to partially unfold said keratin protein, such that a slurry is formed;
   exchanging the non-volatile acid by treatment with a volatile base; and
   forming said keratin slurry into a sheet.

27. A sheet wound dressing formed by the steps comprising:
   providing a keratin slurry, wherein said keratin is primarily Beta keratin, wherein said keratin has a plurality of —$CH_2SH$ groups that will form disulfide linkages within days; and forming said slurry into a sheet, such that said disulfide linkages form.

28. A keratin sheet formed by the steps comprising:

providing a cross-linkable keratin slurry; and forming said slurry into a sheet, such that said keratin cross-links.

29. A keratin sheet as recited in claim 28 wherein said keratin is primarily Beta keratin.

30. A keratin sheet as recited in claim 28 wherein said keratin is at least 10% Beta keratin.

31. A keratin sheet as recited in claim 30 wherein said keratin is at least 80% Beta keratin.

32. A keratin sheet dressing as recited in claim 28 wherein said forming includes casting said keratin onto a flat surface.

33. A keratin sheet dressing as recited in claim 28 wherein said forming includes casting said keratin into a mold of appropriate geometry and surface finish.

* * * * *

UNITED STATES PATENT AND TRADEMARK OFFICE
CERTIFICATE OF CORRECTION

PATENT NO. : 5,948,432
DATED : September 7, 1999
INVENTOR(S) : Scott F. Timmons et al.

It is certified that error appears in the above-identified patent and that said Letters Patent is hereby corrected as shown below:

Column 7, claim 13, line 62, delete "6" please insert --7--

Signed and Sealed this

Fourth Day of July, 2000

Attest:

Q. TODD DICKINSON

Attesting Officer      Director of Patents and Trademarks